US010807978B2

(12) United States Patent
Murugan et al.

(10) Patent No.: US 10,807,978 B2
(45) Date of Patent: Oct. 20, 2020

(54) PROCESS FOR PREPARATION OF PALBOCICLIB

(71) Applicant: DR. REDDY'S LABORATORIES LIMITED, Hyderabad (IN)

(72) Inventors: Andiappan Murugan, Bangalore (IN); Vipinkumar Shriram Kabra, Bengaluru (IN); Chinna Saida Reddy Gade, Bengaluru (IN); Rama Rao Gondu, Andhra Pradesh (IN); Shravankumar Chandrashekar, Bengaluru (IN); Krishnamoorthy Pasupathy, Bengaluru (IN); Anandan Kalaiselvan, Bengaluru (IN)

(73) Assignee: DR. REDDY'S LABORATORIES LIMITED, Hyderabad (IN)

( * ) Notice: Subject to any disclaimer, the term of this patent is extended or adjusted under 35 U.S.C. 154(b) by 0 days.

(21) Appl. No.: 16/314,972

(22) PCT Filed: Jul. 3, 2017

(86) PCT No.: PCT/IB2017/054000
§ 371 (c)(1),
(2) Date: Jan. 3, 2019

(87) PCT Pub. No.: WO2018/007927
PCT Pub. Date: Jan. 11, 2018

(65) Prior Publication Data
US 2019/0241561 A1    Aug. 8, 2019

(30) Foreign Application Priority Data

Jul. 4, 2016 (IN) .............................. 201641022857
Nov. 4, 2016 (IN) .............................. 201641037735
Mar. 30, 2017 (IN) .............................. 201741011366

(51) Int. Cl.
*C07D 471/04* (2006.01)
*C07B 49/00* (2006.01)

(52) U.S. Cl.
CPC ............ *C07D 471/04* (2013.01); *C07B 49/00* (2013.01); *C07B 2200/13* (2013.01)

(58) Field of Classification Search
CPC .................................................... C07D 471/04
See application file for complete search history.

(56) References Cited

U.S. PATENT DOCUMENTS 7,781,583 B2    8/2010    Erdman et al.

FOREIGN PATENT DOCUMENTS

WO    2003/062236 A1    7/2003
WO    2016/030439 A1    3/2016

OTHER PUBLICATIONS

International Search Report dated Nov. 3, 2017, for corresponding International Patent Application No. PCTIIB2017/054000.
Written Opinion dated Nov. 3, 2017, for corresponding International Patent Application No. PCT/IB2017/054000.
International Preliminary Report on Patentability dated Jan. 8, 2019, for corresponding International Patent Application No. PCTIIB2017/054000.

*Primary Examiner* — Brian E McDowell
(74) *Attorney, Agent, or Firm* — Pergament & Cepeda LLP; Milagros A. Cepeda; Edward D. Pergament

(57) ABSTRACT

The present application relates to a process for the preparation of crystalline form A of palbociclib having specific surface area more than 2 m²/g comprising one-pot process for the preparation of compound of formula (IV). The present application further relates to the preparation of acid-addition salts of palbociclib and their use for the synthesis of crystalline form A of palbociclib having specific surface area more than 2 m²/g.

6 Claims, 2 Drawing Sheets

PROCESS FOR PREPARATION OF PALBOCICLIB

This application is a National Stage Application under 35 U.S.C. § 371 of PCT International Application No. PCT/IB2017/054000, filed Jul. 3, 2017, which takes priority from Indian Provisional Application Numbers IN 201641022857, filed Jul. 4, 2016; IN 201641037735, filed on Nov. 4, 2016 and IN 201741011366, filed Mar. 30, 2017, all of which are herein incorporated in its entirety.

FIELD OF INVENTION

The present application relates to process for preparation of palbociclib. The present application further relates to the acid addition salts of palbociclib.

BACKGROUND

Palbociclib is a cylcin-dependent kinase-4 inhibitor indicated for the treatment of postmenopausal women with estrogen receptor (ER)-positive, human epidermal growth factor receptor 2 (HER2)-negative advanced breast cancer as initial endocrine-based therapy for their metastatic disease. Palbociclib is first time known in PCT application number, WO2003062236A1 (hereinafter referred as the WO'236 application). Palbociclib is chemically known as 6-acetyl-8-cyclopentyl-5-methyl-2-{[5-(piperazin-1-yl)pyridin-2yl]amino}-pyrido[2,3-d]pyrimidin-7(8H)-one and has following structural formula:

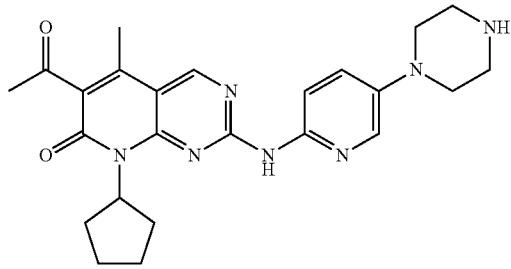 [SMILES: CC(=O)c1c(C)c2cnc(Nc3ccc(N4CCNCC4)cn3)nc2n(C2CCCC2)c1=O]

US Patent, U.S. Pat. No. 7,781,583B2 (hereinafter referred as the US'583 patent) discloses a process for preparation of palbociclib.

There remains a need for a cost-effective and industrially suitable process for preparation of palbociclib.

SUMMARY

First aspect of the present application relates to one-pot process for the preparation of compound of formula (IV) comprising the steps of:
(a) reacting compound of formula (I) with a compound of formula (II) to provide compound of formula (III)

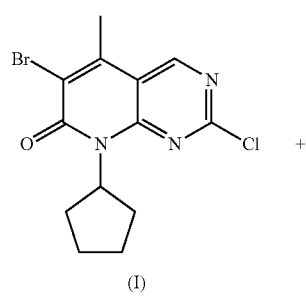

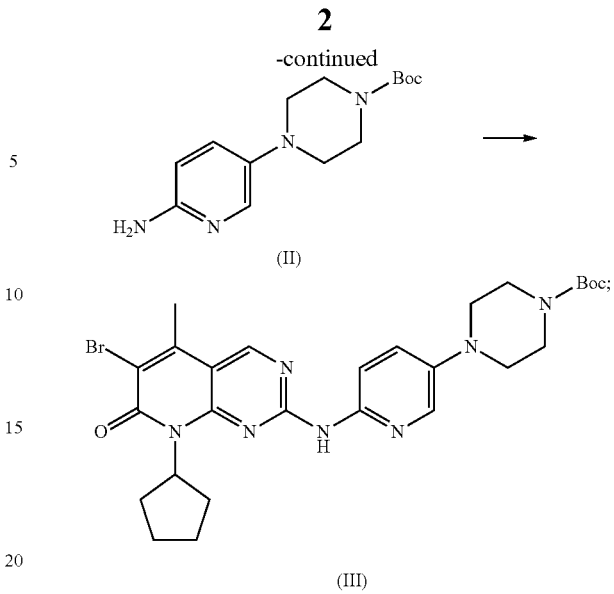

(b) reacting compound of formula (III) with n-butyl vinyl ether to provide compound of formula (IV)

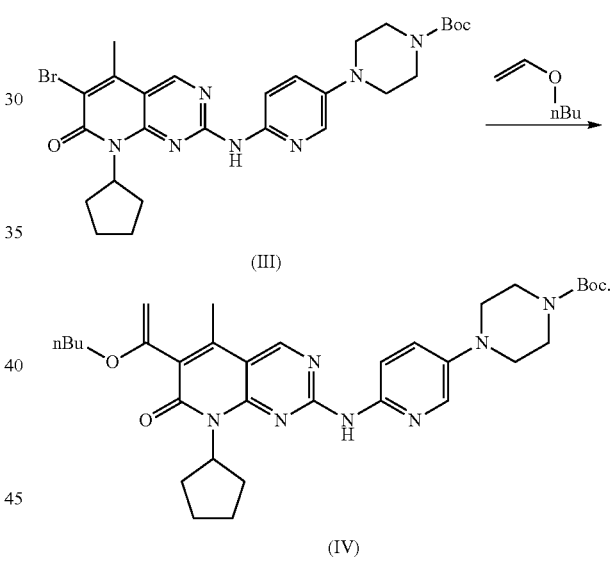

Second aspect of the present application relates to a process for preparation of crystalline form A of palbociclib having specific surface area more than 2 m²/g, comprising
(a) treating compound of formula (IV) with an acid to provide an acid-addition salt of palbociclib;
(b) treating acid-addition salt of palbociclib with a base.

Third aspect of the present application relates to oxalic acid salt of palbociclib.

Fourth aspect of the present application relates to a process for preparation of oxalic acid salt of palbociclib comprising reacting compound of formula (IV) with oxalic acid in a suitable solvent.

Fifth aspect of the present application relates to a process for preparation of palbociclib comprising treating oxalic acid salt of palbociclib with a suitable base.

Sixth aspect of the present application relates to use of oxalic acid salt of palbociclib for the preparation of palbociclib.

Seventh aspect of the present application relates to trifluoroacetic acid salt of palbociclib.

Eighth aspect of the present application relates to a process for preparation of trifluoroacetic acid salt of palbociclib comprising reacting compound of formula (IV) with trifluoroacetic acid in a suitable solvent.

Ninth aspect of the present application relates to a process for preparation of palbociclib comprising treating trifluoroacetic acid salt of palbociclib with a suitable base.

Tenth aspect of the present application relates to use of trifluoroacetic acid salt of palbociclib for the preparation of palbociclib.

Eleventh aspect of the present application relates to pharmaceutical composition comprising crystalline form A of palbociclib having specific surface area more than 2 m²/g, prepared by the process of the present application, and one or more pharmaceutically acceptable excipients.

DETAILED DESCRIPTION

Figure 1:
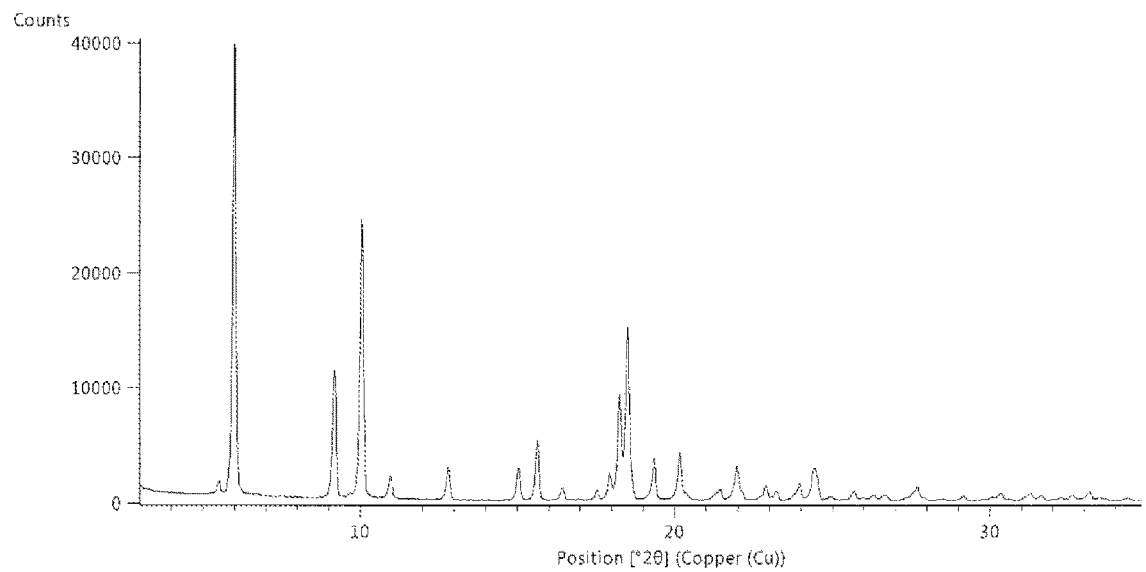
FIG. 1 is an illustration of a PXRD pattern of crystalline form A of compound of formula (V), as obtained by Example 3.

First aspect of the present application relates to one-pot process for the preparation of compound of formula (IV) comprising the steps of:

(a) reacting compound of formula (I) with a compound of formula (II) to provide compound of formula (III)

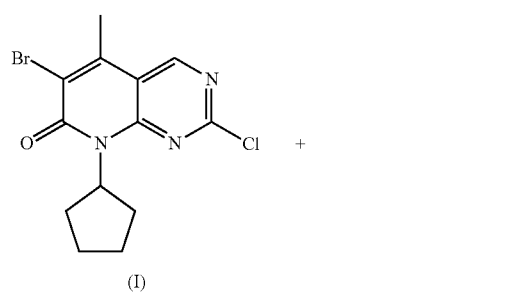

(I)

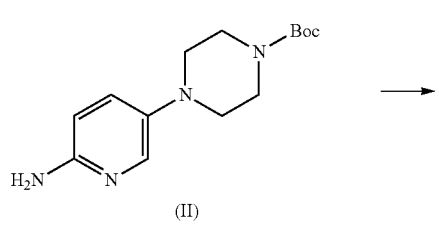

(II)

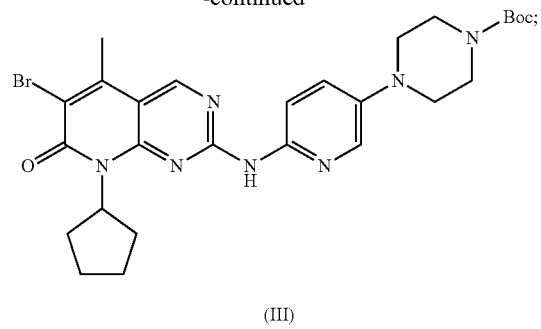

(III)

(b) reacting compound of formula (III) with n-butyl vinyl ether to provide compound of formula (IV)

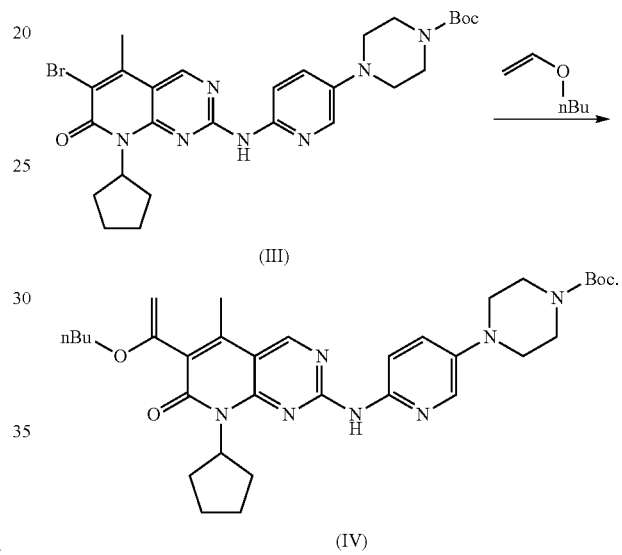

(IV)

In embodiments of step (a), the reaction between compounds of formula (I) with compound of formula (II) may be performed in a suitable solvent in presence of a Grignard reagent. The organic solvent includes but not limited to ether solvent such as tetrahydrofuran, diethyl ether and the like; aromatic hydrocarbon solvent such as benzene, toluene and the like; aliphatic hydrocarbon solvent such as heptane, hexane and the like; chlorinated hydrocarbon solvent such as dichloromethane and the like. Specifically, the solvent may be an ether solvent and more specifically the solvent may be tetrahydrofuran.

Specifically, the Grignard reagent may be isopropyl magnesium chloride. The reaction between compounds of formula (I) and the compound of formula (II) may be carried out for about 30 minutes to about 10 hours at about 0° C. to about boiling point of the solvent.

Specifically, the reaction between compounds of formula (I) and the compound of formula (II) may be carried out for about 1 hour to about 4 hours at about 0° C. to about 15° C. The resulting compound of formula (III) may be carried forward to the next step without isolation from the reaction mass.

In embodiments of step (b), the compound of formula (III) may be reacted with butyl vinyl ether in a suitable solvent in presence of a catalyst and a suitable base to provide compound of formula (IV). The suitable solvent may include but not limited to alcohol solvent such as methanol, ethanol, n-butanol and the like; ketone solvent such as acetone, methyl ethyl ketone and the like; ether solvent such as tetrahydrofuran, diethyl ether and the like. Specifically, the solvent may be an alcohol solvent. More specifically, the solvent may be n-butanol. The catalyst may be any catalyst known in the art. Specifically, the catalyst may be a palladium catalyst. More specifically, the catalyst may be $PdCl_2$ (dppf). The suitable base may be any base known in the art. Specifically, the suitable base may be an organic base. More specifically, the suitable base may be diisopropyl ethylamine. The reaction between compounds of formula (III) and butyl vinyl ether may be carried out for about 30 minutes to about 30 hours at about 0° C. to about boiling point of the solvent. Specifically, the reaction between compounds of formula (III) and butyl vinyl ether may be carried out for about 10 hour to about 20 hours at about 70° C. to about 100° C.

Optionally, the reaction mass may be treated with di-tert-butyl dicarbonate at a temperature of about 20° C. to about 100° C. for a sufficient time. In one embodiment, the reaction mass may be treated with di-tert-butyl dicarbonate at a temperature of about 40° C. to about 50° C. for a period of about 10 minutes to about 1 hour.

The compound of formula (IV) may be isolated from the reaction mass as known in the art. The compound of formula (IV) may be purified by crystallization from an organic solvent or water or mixtures thereof. Specifically, the compound of formula (IV) may be purified by crystallization in a mixture of alcoholic solvent and water. More specifically, the compound of formula (IV) may be purified by crystallization in a mixture of n-butanol, methanol and water. Optionally, seed crystals of compound of formula (IV) may be added to facilitate the crystallization of compound of formula (IV).

The present application also relates to a process for reducing palladium content in compound of formula (IV). The process for reducing palladium content in compound of formula (IV) comprises treating a solution comprising compound of formula (IV) with an aqueous solution of L-cysteine. Specifically, the reaction mass comprising compound of formula (IV), obtained by the process of the present application, may be treated with an aqueous solution of L-cysteine for reducing palladium content.

It is known in the literature that filtration of the compound of formula (III) is difficult due to small particle size and needle shape morphology of the compound. Hence, the one-pot process for the preparation of compound of formula (IV) without isolation compound of formula (III), as described in the present application, is a simple and cost-effective process.

Second aspect of the present application relates to a process for preparation of palbociclib comprising
(a) treating compound of formula (IV) with an acid to provide an acid-addition salt of palbociclib;
(b) treating acid-addition salt of palbociclib with a base.

In one embodiment, the acid used in step (a), may be selected from the group of oxalic acid and trifluoroacetic acid. In another embodiment, the acid used in step a), may be selected from the group of methane sulfonic acid and isethionic acid. The reaction of step a) may be carried out in presence of a suitable solvent. The suitable solvent of step a), may include but not limited to alcohol solvent such as methanol, ethanol, n-butanol and the like; ketone solvent such as acetone, methyl ethyl ketone and the like; ether solvent such as tetrahydrofuran, diethyl ether and the like; ester solvent such as ethyl acetate, butyl acetate and the like; aromatic hydrocarbon solvent such as benzene, toluene and the like; aliphatic hydrocarbon solvent such as heptane, hexane and the like; chlorinated hydrocarbon solvent such as dichloromethane, carbon tetrachloride and the like; water; and mixture thereof. Specifically, the solvent is a mixture of an alcohol solvent and water. The reaction may be carried out for about 30 minutes to about 30 hours at about −10° C. to about boiling point of the solvent. The acid-addition salt of palbociclib may be isolated from the reaction mass by a process known in the art. Specifically, the acid-addition salt of palbociclib may be isolated by filtration.

In embodiments of step (b), the acid-addition salt of palbociclib may be treated with a base in presence of a solvent, including but not limited to, alcohol solvent such as methanol, ethanol, n-butanol and the like; ketone solvent such as acetone, methyl ethyl ketone and the like; ether solvent such as tetrahydrofuran, diethyl ether and the like; ester solvent such as ethyl acetate, butyl acetate and the like; aromatic hydrocarbon solvent such as benzene, toluene and the like; aliphatic hydrocarbon solvent such as heptane, hexane and the like; chlorinated hydrocarbon solvent such as dichloromethane, carbon tetrachloride and the like; water; and mixture thereof. Specifically, the solvent is a mixture of an alcohol solvent and water. More specifically, the solvent may be a mixture of methanol and water. The base includes but not limited to organic base such as triethylamine, diisopropyl ethylamine and the like; inorganic base such as sodium hydroxide, potassium carbonate and the like. Specifically, the base may be an inorganic base. More specifically, the base may be sodium hydroxide. Palbociclib may be isolated from the reaction mass by a process known in the art. Specifically, palbociclib may be isolated by filtration.

Third aspect of the present application relates to oxalic acid salt of palbociclib.

Fourth aspect of the present application relates to a process for preparation of oxalic acid salt of palbociclib comprising reacting compound of formula (IV) with oxalic acid in a suitable solvent.

Fifth aspect of the present application relates to a process for preparation of palbociclib comprising treating oxalic acid salt of palbociclib with a suitable base.

Sixth aspect of the present application relates to use of oxalic acid salt of palbociclib for the preparation of palbociclib.

Seventh aspect of the present application relates to trifluoroacetic acid salt of palbociclib.

Eighth aspect of the present application relates to a process for preparation of trifluoroacetic acid salt of palbociclib comprising reacting compound of formula (IV) with trifluoroacetic acid in a suitable solvent.

Ninth aspect of the present application relates to a process for preparation of palbociclib comprising treating trifluoroacetic acid salt of palbociclib with a suitable base.

Tenth aspect of the present application relates to use of trifluoroacetic acid salt of palbociclib for the preparation of palbociclib.

It has been observed by the inventors of the present application that impurities are formed when an acid-addition salt of palbociclib such as sulfonic acid-addition salt like isethionic acid or mineral acid-addition salt such as hydrochloric acid, hydrobromic acid, hydroiodic acid, phosphoric acid and sulfuric acid is converted to palbociclib free base in presence of alcohol. The inventors have found out that using oxalic acid and trifluoroacetic acid salt of palbociclib as an intermediate for the preparation of palbociclib does not generate impurities even in the presence of alcohol and palbociclib of good quality and purity may be achieved easily using oxalic acid and trifluoroacetic acid salt of palbociclib as intermediate.

Another aspect of the present application relates to a process for the preparation of crystalline form A of palbociclib having specific surface area more than 2 m²/g, comprising the steps of:

(a) reacting compound of formula (I) with a compound of formula (II) to provide compound of formula (III)

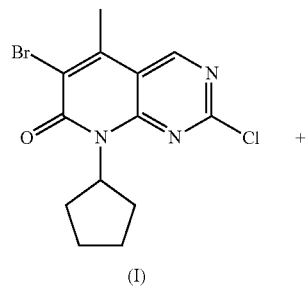

(I)

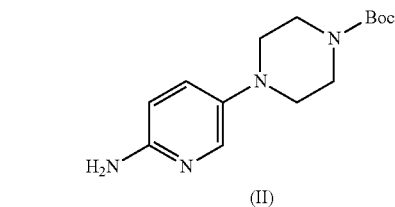

(II)

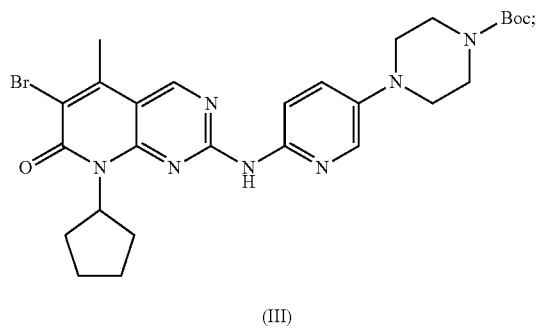

(III)

(b) reacting compound of formula (III) with n-butyl vinyl ether to provide compound of formula (IV)

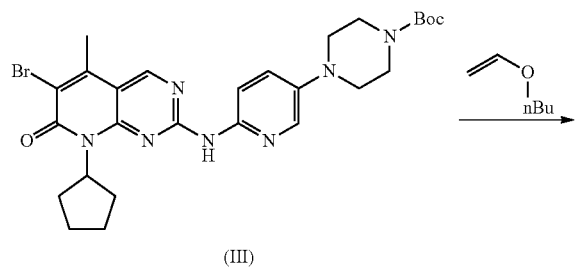

(III)

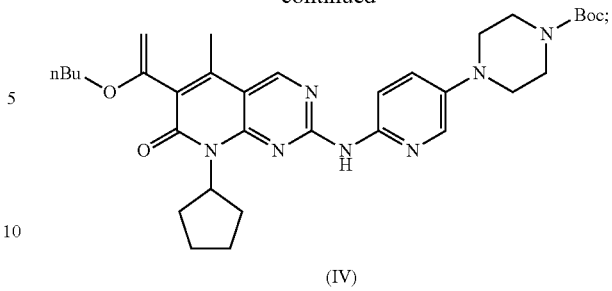

(IV)

(c) reacting compound of formula (IV) with methane sulfonic acid to provide methane sulfonic acid salt of palbociclib of formula (V);

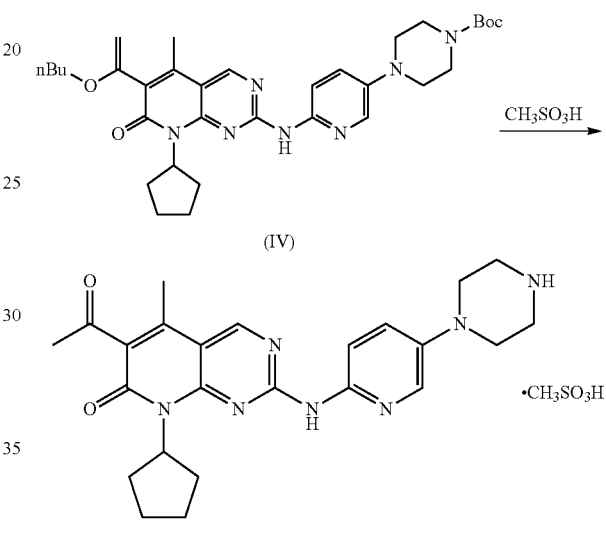

(IV)

(V)

(d) treating methane sulfonic acid salt of palbociclib of formula (V) with aqueous solution of copper acetate to provide pure compound of formula (V)

(e) treating pure compound of formula (V) with a base.

In embodiments of step (a), the reaction between compounds of formula (I) with compound of formula (II) may be performed in a suitable solvent in presence of a Grignard reagent. The organic solvent includes but not limited to ether solvent such as tetrahydrofuran, diethyl ether and the like; aromatic hydrocarbon solvent such as benzene, toluene and the like; aliphatic hydrocarbon solvent such as heptane, hexane and the like; chlorinated hydrocarbon solvent such as dichloromethane and the like. Specifically, the solvent may be an ether solvent and more specifically the solvent may be tetrahydrofuran. Specifically, the Grignard reagent may be isopropyl magnesium chloride. The reaction between compounds of formula (I) and the compound of formula (II) may be carried out for about 30 minutes to about 10 hours at about 0° C. to about boiling point of the solvent. Specifically, the reaction between compounds of formula (I) and the compound of formula (II) may be carried out for about 1 hour to about 4 hours at about 0° C. to about 15° C.

One specific aspect of the present application relates to a process for the preparation of Palbociclib wherein compound of formula (III) is not isolated from the reaction mass and directly carried forward to the next step without isolation.

In embodiments of step (b), the compound of formula (III) may be reacted with butyl vinyl ether in a suitable solvent in presence of a catalyst and a suitable base to provide compound of formula (IV). The suitable solvent may include but not limited to alcohol solvent such as methanol, ethanol, n-butanol, isopropanol and the like; ketone solvent such as acetone, methyl ethyl ketone and the like; ether solvent such as tetrahydrofuran, diisopropyl ether and the like; polar aprotic solvent such as dimethyl formamide, n-methyl pyrrolidine and the like. Specifically, the solvent may be an alcohol solvent. More specifically, the solvent may be n-butanol. The catalyst may be any catalyst known in the art. Specifically, the catalyst may be a palladium catalyst. More specifically, the catalyst may be PdCl2 (dppf). The suitable base may be any base known in the art. Specifically, the suitable base may be an organic base. More specifically, the suitable base may be diisopropyl ethylamine. The reaction between compounds of formula (III) and butyl vinyl ether may be carried out for about 30 minutes to about 30 hours at about 0° C. to about boiling point of the solvent. Specifically, the reaction between compounds of formula (III) and butyl vinyl ether may be carried out for about 10 hour to about 20 hours at about 70° C. to about 100° C.

Optionally, the reaction mass may be treated with di-tert-butyl dicarbonate at a temperature of about 20° C. to about 100° C. for a sufficient time. In one embodiment, the reaction mass may be treated with di-tert-butyl dicarbonate at a temperature of about 40° C. to about 50° C. for a period of about 10 minutes to about 1 hour.

The compound of formula (IV) may be isolated from the reaction mass as known in the art. The compound of formula (IV) may be purified by crystallization in an organic solvent, water and mixtures thereof. Specifically, the compound of formula (IV) may be purified by crystallization in a mixture of alcoholic solvent and water. More specifically, the compound of formula (IV) may be purified by crystallization in a mixture of n-butanol, methanol and water. Optionally, seed crystals of compound of formula (IV) may be added to facilitate the crystallization of compound of formula (IV).

The present application also relates to a process for reducing palladium content in compound of formula (IV). The process for reducing palladium content in compound of formula (IV) comprises treating a solution comprising compound of formula (IV) with an aqueous solution of L-cysteine. Specifically, the reaction mass comprising compound of formula (IV), obtained by the process of the present application, may be treated with an aqueous solution of L-cysteine for reducing palladium content.

In embodiments of step c), the compound of formula (IV) may be reacted with methane sulfonic acid for the preparation of compound of formula (V) in a solvent including but not limited to alcohol solvent such as methanol, ethanol, n-butanol, isopropanol and the like; ketone solvent such as acetone, methyl ethyl ketone and the like; ether solvent such as tetrahydrofuran, diisopropyl ether and the like; hydrocarbon solvent such as hexane, toluene and the like; water and mixture thereof. Specifically, the solvent may be a mixture of an alcohol solvent and water. More specifically, the alcohol solvent may be methanol. The reaction between compound of formula (IV) and methane sulfonic acid may be carried out at about −10° C. to about boiling point of the solvent for sufficient time. Specifically, reaction between compound of formula (IV) and methane sulfonic acid may be carried out at about 40° C. to about 60° C. of the solvent for a period of about 15 minutes to about 5 hours. Optionally, the reaction may be seeded with pure sample of compound of formula (V). The compound of formula (V) may be isolated from the reaction mass by any method known in the art. Specifically, the compound of formula (V) may be isolated from the reaction mass by filtration.

In embodiments of step d), a process for the preparation of pure compound of formula (V) comprising treating compound of formula (V) with an aqueous solution of copper acetate. The compound of formula (V) may be treated with an aqueous solution of copper acetate at a temperature of about 0° C. to about 100° C. for a sufficient time. Specifically, the compound of formula (V) may be treated with an aqueous solution of copper acetate at a temperature of about 0° C. to about 100° C. for about 1 hour to about 24 hours. More specifically, the compound of formula (V) may be treated with an aqueous solution of copper acetate at a temperature of about 50° C. to about 60° C. for about 10 hours to about 15 hours. The reaction mass may optionally be treated with methane sulfonic acid for about 10 minutes to about 1 hours at a temperature of about 15 minutes to about 1 hour. The reaction mass may be optionally seeded with pure compound of formula (V). The compound of formula (V) may be isolated from the reaction mass by any method known in the art. Specifically, the compound of formula (V) may be isolated from the reaction mass by filtration.

The compound of formula (V) may optionally be crystallized in order to afford more pure compound. The solvent for crystallization may include but not limited to alcohol solvent such as methanol, ethanol, n-butanol, isopropanol and the like; ketone solvent such as acetone, methyl ethyl ketone and the like; ether solvent such as tetrahydrofuran, diisopropyl ether and the like; hydrocarbon solvent such as hexane, toluene and the like; water and mixture thereof. Specifically, the solvent may be a mixture of alcohol solvent and water. More specifically, the alcohol solvent may be methanol.

Another aspect of the present application relates to a crystalline form A of compound of formula (V) characterized by a PXRD pattern substantially as illustrated in FIG. 1.

Figure 2:
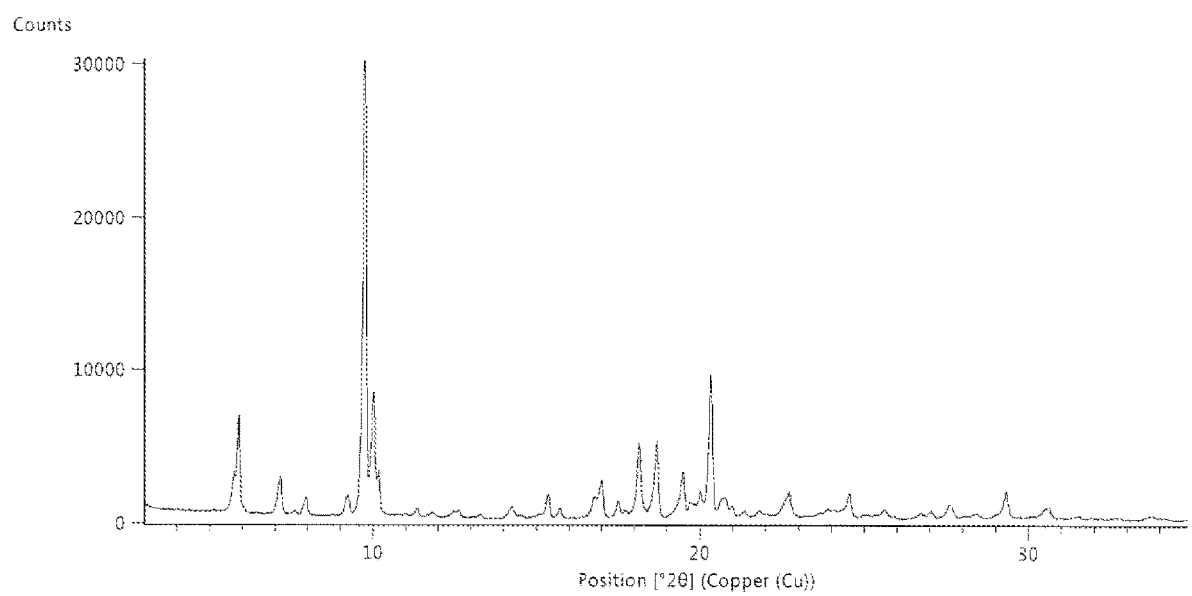
FIG. 2 is an illustration of a PXRD pattern of crystalline form B of compound of formula (V), as obtained by Example 4.
Figure 3:
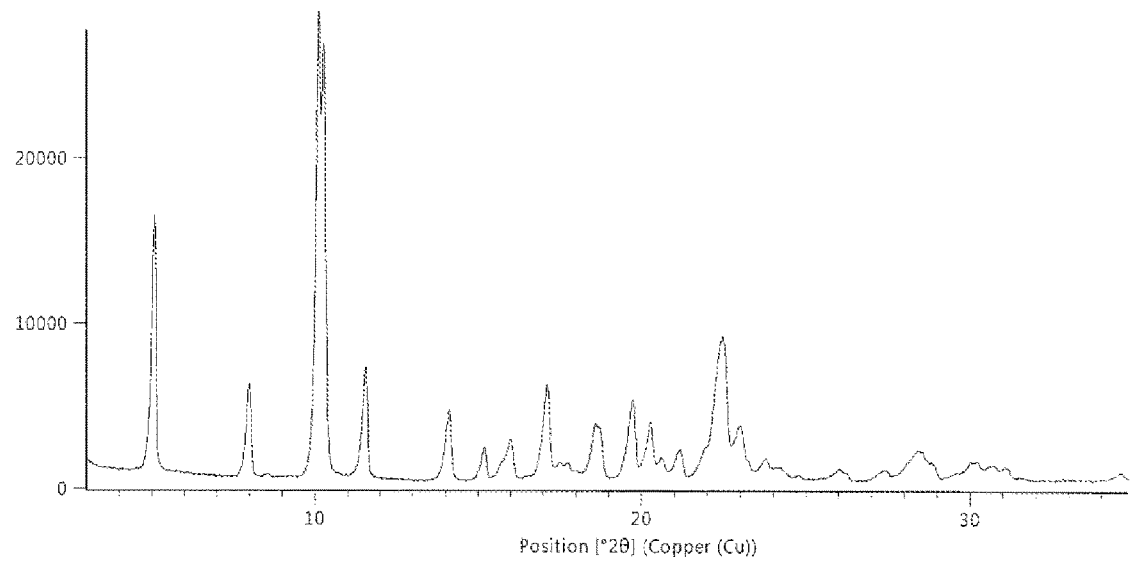
FIG. 3 is an illustration of PXRD pattern of crystalline form A of palbociclib, as obtained by example 9.

Yet another aspect of the present application relates to a crystalline form B of compound of formula (V) characterized by a PXRD pattern substantially as illustrated in FIG. 2.

In embodiments of step (e), the compound of formula (V) may be treated with a base in solvent including but not limited to alcohol solvent such as methanol, ethanol, n-butanol, isopropanol and the like; ketone solvent such as acetone, methyl ethyl ketone and the like; ether solvent such as tetrahydrofuran, diisopropyl ether and the like; hydrocarbon solvent such as hexane, toluene and the like; ester solvent such as ethyl acetate, isopropyl acetate and the like; water and mixture thereof. Specifically, the solvent may be a mixture of alcohol solvent and water. More specifically, the alcohol solvent may be methanol. The base may include but not limited to inorganic base such as sodium hydroxide, potassium hydroxide, sodium carbonate, potassium carbonate and the like; organic base such as triethylamine, diisopropyl ethylamine and the like. Specifically, the base may be an inorganic base. More specifically, the base may be sodium hydroxide. Crystalline form A of palbociclib having specific surface area more than 2 $m^2/g$ may be isolated from the reaction mass by any method known in the art. Specifically, crystalline form A of palbociclib having specific surface area more than 2 $m^2/g$ may be isolated by filtration.

Eleventh aspect of the present application relates to pharmaceutical composition comprising crystalline form A of palbociclib having specific surface area more than 2 $m^2/g$, prepared by the process of the present application, and one or more pharmaceutically acceptable excipients.

Crystalline form A of palbociclib having specific surface area more than 2 m$^2$/g, prepared by the process of the present application, together with one or more pharmaceutically acceptable excipients of the present application may be formulated as: solid oral dosage forms such as, but not limited to, powders, granules, pellets, tablets, and capsules; liquid oral dosage forms such as, but not limited to, syrups, suspensions, dispersions, and emulsions; and injectable preparations such as, but not limited to, solutions, dispersions, and freeze dried compositions. Formulations may be in the forms of immediate release, delayed release, or modified release. Further, immediate release compositions may be conventional, dispersible, chewable, mouth dissolving, or flash melt preparations, and modified release compositions that may comprise hydrophilic or hydrophobic, or combinations of hydrophilic and hydrophobic, release rate controlling substances to form matrix or reservoir or combination of matrix and reservoir systems. The compositions may be prepared using any one or more of techniques such as direct blending, dry granulation, wet granulation, and extrusion and spheronization. Compositions may be presented as uncoated, film coated, sugar coated, powder coated, enteric coated, and modified release coated.

Pharmaceutically acceptable excipients that are useful in the present application include, but are not limited to: diluents such as starches, pregelatinized starches, lactose, powdered celluloses, microcrystalline celluloses, dicalcium phosphate, tricalcium phosphate, mannitol, sorbitol, sugar, and the like; binders such as acacia, guar gum, tragacanth, gelatin, polyvinylpyrrolidones, hydroxypropyl celluloses, hydroxypropyl methyl celluloses, pregelatinized starches, and the like; disintegrants such as starches, sodium starch glycolate, pregelatinized starches, crospovidones, croscarmellose sodium, colloidal silicon dioxide, and the like; lubricants such as stearic acid, magnesium stearate, zinc stearate, and the like; glidants such as colloidal silicon dioxide and the like; solubility or wetting enhancers such as anionic, cationic, or neutral surfactants; complex forming agents such as various grades of cyclodextrins and resins; and release rate controlling agents such as hydroxypropyl celluloses, hydroxymethyl celluloses, hydroxypropyl methylcelluloses, ethylcelluloses, methylcelluloses, various grades of methyl methacrylates, waxes, and the like. Other pharmaceutically acceptable excipients that are useful include, but are not limited to, film formers, plasticizers, colorants, flavoring agents, sweeteners, viscosity enhancers, preservatives, antioxidants, and the like.

Definitions

The following definitions are used in connection with the present application unless the context indicates otherwise.

The terms "about," "general, 'generally,'" and the like are to be construed as modifying a term or value such that it is not an absolute. Such terms will be defined by the circumstances and the terms that they modify as those terms are understood by those of skill in the art. This includes, at very least, the degree of expected experimental error, technique error and instrument error for a given technique used to measure a value.

A name used herein to characterize a crystalline form should not be considered limiting with respect to any other substance possessing similar or identical physical and chemical characteristics, but rather it should be understood that these designations are mere identifiers that should be interpreted according to the characterization information also presented herein.

All percentages and ratios used herein are by weight of the total composition and all measurements made are at about 25° C. and about atmospheric pressure, unless otherwise designated. All temperatures are in degrees Celsius unless specified otherwise. As used herein, the terms "comprising" and "comprises" mean the elements recited, or their equivalents in structure or function, plus any other element or elements which are not recited. The terms "having" and "including" are also to be construed as open ended. All ranges recited herein include the endpoints, including those that recite a range between two values. Whether so indicated or not, all values recited herein are approximate as defined by the circumstances, including the degree of expected experimental error, technique error, and instrument error for a given technique used to measure a value.

The term "optional" or "optionally" is taken to mean that the event or circumstance described in the specification may or may not occur, and that the description includes instances where the event occurs and instances where it does not.

In general, a diffraction angle (2θ) in powder X-ray diffractometry may have an error in the range of ±0.2°. Therefore, the aforementioned diffraction angle values should be understood as including values in the range of about ±0.2°. Accordingly, the present application includes not only crystals whose peak diffraction angles in powder X-ray diffractometry completely coincide with each other, but also crystals whose peak diffraction angles coincide with each other with an error of about ±0.2°. Therefore, in the present specification, the phrase "having a diffraction peak at a diffraction angle (2θ+0.2°) of 19.6°" means "having a diffraction peak at a diffraction angle (2θ) of 19.4° to 19.8°. Although the intensities of peaks in the x-ray powder diffraction patterns of different batches of a compound may vary slightly, the peaks and the peak locations are characteristic for a specific polymorphic form. The relative intensities of the PXRD peaks can vary depending on the sample preparation technique, crystal size distribution, various filters used, the sample mounting procedure, and the particular instrument employed. Moreover, instrument variation and other factors can affect the 2-theta values.

Certain specific aspects and embodiments of the present application will be explained in greater detail with reference to the following examples, which are provided only for purposes of illustration and should not be construed as limiting the scope of the disclosure in any manner.

EXAMPLES

Example 1: Preparation of tert-butyl 4-(6-((6-(1-butoxyvinyl)-8-cyclopentyl-5-methyl-7-oxo-7,8-dihydropyrido[2,3-d]pyrimidin-2-yl)amino)pyridin-3-yl)piperazine-1-carboxylate (IV)

To a solution of 6-bromo-2-chloro-8-cyclopentyl-5-methylpyrido[2,3-d]pyrimidin-7(8H)-one (I) (25 g) and tert-butyl 4-(6-aminopyridin-3-yl)piperazine-1-carboxylate (II) (24.5 g) in tetrahydrofuran (125 mL) at −10° C. under nitrogen atmosphere, a solution of isopropyl magnesium chloride in tetrahydrofuran (2 M, 150 mL) was added slowly for a period of about 45 minutes such that the temperature of the reaction mass was maintained less than 10° C. The reaction mass was stirred at 0-10° C. for 1.5 hours and again a solution of isopropyl magnesium chloride in tetrahydrofuran (2 M, 5 mL) was added slowly over a period of 5 minutes.

The reaction mass was stirred for 1 hour and quenched by the slow addition of n-butanol (150 mL). The organic solvent was distilled under vacuum at about 50° C. and further added n-butanol (245 mL). The reaction mass was heated to 95° C. and PdCl$_2$(dppf) (3.29 g) was added to the reaction mass, followed by diisopropylethyl amine (50.8 mL) and butyl vinyl ether (56.6 mL). The reaction mass was heated at 95° C. maintained at that temperature for 16 hours under nitrogen atmosphere. The reaction mass was cooled to about 65-70° C. The reaction mass was added to water (800 mL). The pH of the reaction mass was adjusted to 7.4-80 by the addition of aqueous solution of acetic acid (20%) at about 65° C. and stirred for 10 minutes. The organic layer was separated and washed with pre-heated aqueous L-cysteine solution (0.55% w/v, 2×800 mL) by reverse charging of organic layer to the aqueous L-cysteine solution at about 65° C. to remove palladium metal from the reaction mass. The combined aqueous layer was extracted with n-butanol (1×50 mL). To half of the organic layer, water (100 mL) and methanol (375 mL) were added slowly and stirred for 10 minutes at about 60° C. The reaction mass was slowly cooled to about 45° C., seeded with reference standard product and further water (100 mL) was added. The reaction mass was stirred for 1 hour at the same temperature, the precipitated solid was filtered and washed with aqueous methanol (50% v/v, 100 mL). The solid was dried at 65° C. overnight to afford the title compound.

Yield: 29 g
Purity (By HPLC): 94.67%

Example 2: Preparation of tert-butyl 4-(6-((6-(1-butoxyvinyl)-8-cyclopentyl-5-methyl-7-oxo-7,8-dihydropyrido[2,3-d]pyrimidin-2-yl)amino)pyridin-3-yl)piperazine-1-carboxylate (IV)

To a mixture of 6-bromo-2-chloro-8-cyclopentyl-5-methylpyrido[2,3-d]pyrimidin-7(8H)-one (I) (50 g) and tert-butyl 4-(6-aminopyridin-3-yl)piperazine-1-carboxylate (II) (48.7 g) in tetrahydrofuran (250 mL) at −5° C. under nitrogen atmosphere, a solution of isopropyl magnesium chloride in tetrahydrofuran (2 M, 150 mL) was added slowly for a period of about 90 minutes such that the temperature of the reaction mass was maintained less than 5° C. The reaction mass was stirred at 0-10° C. for 2 hours and quenched by the slow addition of n-butanol (150 mL). Tetrahydrofuran was distilled at about 54° C. and further added n-butanol (200 mL). The reaction mass was heated to 96° C. for 15 minutes and cooled to 70-72° C. At this temperature, PdCl$_2$(dppf) (2.98 g) was added to the reaction mass, followed by diisopropylethyl amine (50.8 mL) and butyl vinyl ether (56.6 mL). The reaction mass was heated at 95-100° C. maintained at that temperature for 12 hours. The reaction mass was cooled to about 45-50° C. and di-tert-butyl dicarbonate (33 mL) was added slowly over a period of 15 minutes. The reaction mass was maintained at 45-50° C. for 50 minutes. In a separate reaction vessel, a solution of L-cysteine (8.84 g) in water (800 mL) was heated to 60-70° C. The reaction mass was added to the aqueous solution and n-butanol (50 mL) was used to rinse the reaction vessel and added further to the aqueous solution. The reaction mass was stirred at about 62° C. and an aqueous solution of acetic acid (20%, 50 mL) was added to the reaction mass. The reaction mass was stirred at 62° C. for 15 minutes and the organic layer was separated from the aqueous layer. Aqueous methanol (20%, 450 mL) was added to the reaction mass and the organic layer was cooled to 45-50° C. The reaction mass was seeded with reference standard product and further aqueous methanol (20%, 500 mL) was added to the reaction mass. The reaction mass was allowed to cool to 0-5° C. over a period of 1 hour and maintained at the same temperature for 1-2 hours. The precipitated product was filtered, washed with aqueous methanol (20%, 100 mL). The product was dried in a vacuum tray drier for about 19 hours at 50° C. to provide the title compound.

Yield: 66 g
Purity (By HPLC): 96.49%

Example 3: Preparation of Crystalline Form A of Methane Sulfonic Acid Salt of Palbociclib (V)

A mixture of compound of formula (IV) (170 g), methanol (1700 mL) and water (170 mL) was cooled to 0-5° C. Methane sulfonic acid (91.4 mL) was added slowly to the above mixture and the reaction mass was heated to 55-60° C. The reaction mass was stirred at that temperature for about 3 hours and then cooled to 4-45° C. for 30 minutes. A seed of pure compound of formula (V) (1.7 g) was added to the reaction mass which was further cooled to −2 to 3° C. for 45 minutes and maintained at that temperature for 1 hour. The precipitated material was filtered, washed with chilled methanol (170 mL) and suck-dried for 10 minutes. The solid was dried in vacuum-tray drier for 30 minutes as 50° C.

In a mixture of copper acetate (5.6 g) in water (102 mL), the above solid was added at 35-40° C. A further quantity of water (68 mL) was added to the reaction mass and maintained at 55-60° C. for 14 hours. Methanol (1700 mL) was added to the reaction mass and cooled to 30-35° C. Methane sulfonic acid (54.8 mL) was added to the reaction mass. A pure sample of compound of formula (V) (1.7 g) was added as seeding material to the reaction mass and the reaction mass was maintained at the same temperature for about 30 minutes. The reaction mass was further cooled to 0-5° C. for 30 minutes and maintained at that temperature for 1 hour. The precipitated product was filtered, washed with chilled methanol (170 mL) and suck-dried for 10 minutes. The solid was dried in vacuum tray drier for 30 minutes at 50° C. to provide the title compound.

Yield: 136 g
Purity (by HPLC): 99.55%

Example 4: Preparation of Crystalline Form B of Methane Sulfonic Acid Salt of Palbociclib (V)

The compound of formula (V), as obtained in example 2 (135 g), was mixed with methanol (1360 mL) and water (85 mL). The reaction mass was heated for 30 minutes at 55-60° C. Methane sulfonic acid (36 mL) was added to the reaction mass at that temperature and the reaction mass was cooled to 40-50° C. The reaction mass was seed with a pure sample of compound of formula (V) (1.7 g) and maintained at the same temperature for 30 minutes. The reaction mass further cooled to 0-5° C. and maintained at the same temperature for 1 hour. The precipitated material was filtered, washed with chilled methanol (100 mL) and suck-dried for 10 minutes. The solid was dried under vacuum at 54° C. for 15 hours to afford the desired compound.

Yield: 122.5 g
Purity (by HPLC): 99.66%

Example 5: Preparation of Oxalic Acid Salt of Palbociclib

To a mixture of tert-butyl 4-(6-((6-(1-butoxyvinyl)-8-cyclopentyl-5-methyl-7-oxo-7,8-dihydropyrido[2,3-d]pyrimidin-2-yl)amino)pyridin-3-yl)piperazine-1-carboxylate (IV) (20 g), isopropyl alcohol (140 mL) and water (60 mL), oxalic acid (20.88 g) was added and the reaction mass was heated up to 81° C. The reaction mass was stirred at the same temperature for about 22 hours and then cooled to 0-5° C. The precipitated solid was filtered and washed with aqueous isopropyl alcohol (30%, 60 mL). The solid was dried overnight at 50° C. under vacuum to provide the desired compound.

Yield: 16.8 g
Purity (By HPLC): 97.12%

Example 6: Preparation of Trifluoroacetic Acid Salt of Palbociclib

To a mixture of tert-butyl 4-(6-((6-(1-butoxyvinyl)-8-cyclopentyl-5-methyl-7-oxo-7,8-dihydropyrido[2,3-d]pyrimidin-2-yl)amino)pyridin-3-yl)piperazine-1-carboxylate (IV) (14 g), methanol (140 mL) and water (4.2 mL), trifluoroacetic acid (8.9 mL) was added and the reaction mass was heated to 55° C. and stirred for 28 hours. Another lot of trifluoroacetic acid (6 mL) was added and the reaction mass was stirred for 40 hours at 55° C. Water (30 mL) was added to the reaction mass the temperature raised to 70° C. The reaction mass was stirred at 70° C. for about 5 hours. Third lot of trifluoroacetic acid (5 mL) was added to the reaction mass and continued stirring for about 4 hours at 70° C. Another lot of trifluoroacetic acid (5 mL) was added and the reaction mass was stirred at 60° C. for 5 hours. The reaction mass was distilled completely and stripped off with isopropyl alcohol (2×70 mL). Aqueous isopropyl alcohol (10%, 140 mL) was added to the reaction mass and cooled to 20-25° C. and stirred for 2 hours. The precipitated solid was filtered and washed with isopropyl alcohol (70 mL). The solid was dried at 50° C. under vacuum to afford the desired compound.

Yield: 9 g
Purity (By HPLC): 98.78%

Example 7: Preparation of Palbociclib

A mixture of oxalic acid salt of palbociclib (2 g), water (12 mL) and methanol (8 mL) was heated to 40° C. and the pH of the heterogeneous reaction mass was adjusted to 9.5-10.0 using aqueous solution of sodium hydroxide (1N). The reaction mass was cooled to 20-25° C. and the precipitated solid was filtered. The solid was washed with water (10 mL) and methanol (10 mL). The solid was dried at 50° C. under vacuum to provide the title compound.

Yield: 1.6 g
Purity (By HPLC): 99.16%

Example 8: Preparation of Palbociclib

A mixture of trifluoroacetic acid salt of palbociclib (4 g), water (24 mL) and methanol (16 mL) was heated to 40° C. and the pH of the heterogeneous reaction mass was adjusted to 9.5-10.0 using aqueous solution of sodium hydroxide (1N). The reaction mass was cooled to 20-25° C. and the precipitated solid was filtered. The solid was washed with water (20 mL) and methanol (20 mL). The solid was dried at 50° C. under vacuum to provide the title compound.

Yield: 2.6 g
Purity (By HPLC): 99.1%

Example 9: Preparation of Palbociclib

A mixture of the compound of formula (V) (110 g) and water (550 mL) was stirred at 31° C. for 20 minutes and filtered through hyflow. The residue was washed with water (220 mL) and ethyl acetate (550 mL) was added to the filtrate. The reaction mass was stirred for 15 minutes. The layers were separated and methanol (440 mL) was added to the aqueous layer.

The reaction mass was heated to 40° C. and the pH was adjusted to 6.3 with aqueous solution of sodium hydroxide (1M, 220 mL) in a period of about 10 minutes. Further the pH of the reaction mass was adjusted to 11 with aqueous solution of sodium hydroxide (1M, 280 mL) in a period of about 10 minutes. The reaction mass was maintained at the same temperature for 1 hour and the precipitated solid was filtered. The solid was washed with water (220 mL), followed by methanol (220 mL) and suck-dried for 45 minutes. The compound was dried in a vacuum oven at 65° C. for 13 hours.

Yield: 72 g
Purity (by HPLC): 99.82%
Surface Area (BET method): 3.61 $m^2/g$

Example 10: Preparation of Isethionic Acid Salt of Palbociclib

A mixture of tert-butyl 4-(6-((6-(1-butoxyvinyl)-8-cyclopentyl-5-methyl-7-oxo-7,8-dihydropyrido[2,3-d]pyrimidin-2-yl)amino)pyridin-3-yl)piperazine-1-carboxylate (IV) (80 g) in methanol (720 mL) and water (24 mL) was heated to 55° C. Isethionic acid (46 mL) was slowly added to the above reaction mass at 55° C. for about 15 minutes. The reaction mass was maintained at 58° for about 15 hours. The above reaction mass was slowly cooled to cooled to 25-30° C. The precipitated solid was then filtered, washed with a mixture of 5% water in methanol and dried at 25° C. To the resulting wet material was added water (80 mL) and methanol (720 mL) at 25° C. The reaction mass was heated to 60° C. and maintained for about 15 minutes. The reaction mass was then slowly cooled to 15° C. The precipitated solid was then filtered, washed with a mixture of 10% water in methanol (80 mL) and dried at 15° C. for about 15 minutes. The resulting wet solid was further dried at 50° C. for about 2 hours to afford the title compound.

Yield: 62.3 g
Purity (By HPLC): 99.95%

Example 11: Preparation of Palbociclib

A mixture of isethionic acid salt of palbociclib (54 g) and water (270 mL) was stirred at 25° C. for about 10 minutes. To the above reaction mass was added methanol (172 mL) at 25° C. and stirred for about 5 minutes. The above reaction mass was then filtered through hyflow and washed with a mixture of 50% water in methanol (108 mL). The above filtrate was heated to 35° C. and pH was adjusted to 10.0 using aqueous solution of sodium hydroxide (1N, 155 mL). The reaction mass was cooled to 20-25° C. and the precipitated solid was filtered. The solid was washed with water (108 mL) and methanol (108 mL), dried at 25° C. for 15 hours. The resulting wet solid was further dried at 50° C. for about 10 hours to provide the title compound.

Yield: 32.2 g
Purity (by HPLC): 99.90%
Surface Area (BET method): 9.38 $m^2/g$

Reference Example: Process for preparation of tert-butyl 4-(6-((6-bromo-8-cyclopentyl-5-methyl-7-oxo-7,8-dihydropyrido[2,3-d]pyrimidin-2-yl)amino)pyridin-3-yl)piperazine-1-carboxylate (III)

A solution of 6-bromo-2-chloro-8-cyclopentyl-5-methyl-pyrido[2,3-d]pyrimidin-7(8H)-one (I) (30 g) and tert-butyl 4-(6-aminopyridin-3-yl)piperazine-1-carboxylate (II) (26 g) in tetrahydrofuran (125 mL) was cooled to 10° C. A solution of isopropyl magnesium chloride in tetrahydrofuran (2 M, 150 mL) was added slowly to the above reaction mass for a period of about 90 minutes such that the temperature of the reaction mass was maintained about 10° C. The reaction mass was stirred for 2 hours at the same temperature. A mixture of tetrahydrofuran (60 mL) and acetic acid (15 mL) was added to the above reaction mass at 10° C. The temperature of the above reaction mass was raised to 25-30° C. and allowed for 10 minutes at the same temperature. The reaction mass was then filtered (Filtration time: 1 hour) and washed with methanol (150 mL) and dried for 10 minutes at 10° C. The resulting wet solid was further dried in vacuum tray dryer (VTD) at 50° C. for about 16 hours to provide the title compound.

Yield: 41.1 g

Purity (by HPLC): 92.10%

The invention claimed is:

1. A one-pot process for the preparation of a compound of formula (IV) comprising the steps of:
   (a) reacting compound of formula (I) with a compound of formula (II) to provide a compound of formula (III)

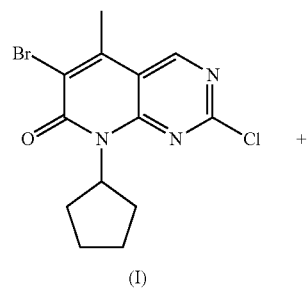

(b) reacting a compound of formula (III) with n-butyl vinyl ether to provide a compound of formula (IV)

2. The process of claim 1, wherein step (a) is carried out in the presence of a Grignard reagent.

3. The process of claim 1, wherein step (b) is carried out in the presence of a palladium catalyst and a base.

4. The process of claim 3, wherein the palladium catalyst is PdCl$_2$(dppf).

5. The process of claim 3, wherein the base is diisopropyl ethylamine.

6. The process of claim 1, wherein the compound of formula (IV) is treated with an aqueous solution of L-cysteine.

* * * * *